United States Patent
Liu et al.

(10) Patent No.: US 10,729,781 B2
(45) Date of Patent: Aug. 4, 2020

(54) LGR4 SPECIFIC MONOCLONAL ANTIBODIES AND METHODS OF THEIR USE

(71) Applicant: THE BOARD OF REGENTS OF THE UNIVERSITY OF TEXAS SYSTEM, Austin, TX (US)

(72) Inventors: Qingyun Liu, Houston, TX (US); Xing Gong, Houston, TX (US); Kendra Carmon, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 34 days.

(21) Appl. No.: 16/062,386

(22) PCT Filed: Dec. 9, 2016

(86) PCT No.: PCT/US2016/065788
§ 371 (c)(1),
(2) Date: Jun. 14, 2018

(87) PCT Pub. No.: WO2017/106034
PCT Pub. Date: Jun. 22, 2017

(65) Prior Publication Data
US 2018/0369403 A1    Dec. 27, 2018

Related U.S. Application Data

(60) Provisional application No. 62/267,409, filed on Dec. 15, 2015.

(51) Int. Cl.
| | | |
|---|---|---|
| *A61K 39/395* | (2006.01) |
| *A61K 47/68* | (2017.01) |
| *C07K 16/28* | (2006.01) |
| *C07K 16/30* | (2006.01) |
| *G01N 33/50* | (2006.01) |
| *G01N 33/543* | (2006.01) |
| *A61P 35/00* | (2006.01) |
| *A61K 39/00* | (2006.01) |

(52) U.S. Cl.
CPC .... *A61K 47/6803* (2017.08); *A61K 39/39558* (2013.01); *A61K 47/6849* (2017.08); *A61P 35/00* (2018.01); *C07K 16/28* (2013.01); *G01N 33/50* (2013.01); *G01N 33/54366* (2013.01); *A61K 2039/505* (2013.01); *C07K 2317/77* (2013.01); *C07K 2317/92* (2013.01)

(58) Field of Classification Search
None
See application file for complete search history.

(56) References Cited

U.S. PATENT DOCUMENTS

2013/0231465 A1    9/2013    Zeidler et al.

FOREIGN PATENT DOCUMENTS

| WO | WO 2006/103116 A1 | 10/2006 |
| WO | WO 2013/067057 A1 | 5/2013 |
| WO | WO 2015/032906 A2 | 3/2015 |

OTHER PUBLICATIONS

International Preliminary Report on Patentability in International Application No. PCT/US2016/065788, dated Jun. 28, 2018.
International Search Report and Written Opinion in International Application No. PCT/US16/65788, dated Apr. 28, 2017.

*Primary Examiner* — Christine J Saoud
*Assistant Examiner* — Jon M Lockard
(74) *Attorney, Agent, or Firm* — Parker Highlander PLLC

(57) ABSTRACT

Isolated or recombinant anti-LGR4 monoclonal antibodies are provided. In some cases, antibodies of the embodiments can be used for the detection, diagnosis and/or therapeutic treatment of human diseases, such as cancer.

11 Claims, 8 Drawing Sheets
Specification includes a Sequence Listing.

SEQUENCE LISTING

```
<160> NUMBER OF SEQ ID NOS: 20

<210> SEQ ID NO 1
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 1

Gln Val Gln Leu Gln Gln Ser Gly Ala Glu Leu Val Lys Pro Gly Ala
1               5                   10                  15

Ser Val Asn Leu Ser Cys Lys Thr Ser Gly Tyr Thr Phe Ser Thr Ser
            20                  25                  30

Tyr Met Ser Trp Phe Lys Gln Ile Pro Gly Gln Thr Ile Glu Trp Val
        35                  40                  45

Gly Leu Ile Tyr Val Gly Ala Gly Gly Pro Thr Tyr Asn Gln Lys Phe
    50                  55                  60

Lys Gly Lys Ala Ser Leu Thr Val Asp Thr Ser Ser Ser Thr Ala Tyr
65                  70                  75                  80

Met Asp Leu Ser Ser Leu Thr Ala Glu Asp Ser Ala Val Tyr Phe Cys
                85                  90                  95

Ala Arg Val Arg Gly Tyr Ala Met Asp Ala Trp Gly Gln Gly Thr Ser
            100                 105                 110

Val Thr Val Ser Ser
        115

<210> SEQ ID NO 2
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 2
caggtccagc tgcagcaatc tggggctgag ttggtaaagc ctggtgcttc agtgaatttg      60
tcctgcaaga cttctggtta caccttcagc actagctaca tgagttggtt caagcagatt     120
cctggacaga ctattgagtg ggttggactg atttatgttg gagctggtgg tcctacctat     180
aatcagaagt tcaagggcaa ggcctcactt actgtcgaca catcttccag cacagcgtac     240
atggatctca gcagcctgac agctgaggac tctgcagtct attttgtgc aagggttcgg      300 ggctatgcta tggatgcctg gggtcaagga acttcagtca ccgtctcctc a              351

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3
```

Gly Tyr Thr Phe Ser Thr Ser Tyr
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic peptide

<400> SEQUENCE: 4

Ile Tyr Val Gly Ala Gly Gly Pro
1               5

<210> SEQ ID NO 5
<211> LENGTH: 10
<212> TYPE: PRT
<213> ORGANISM: Artificial sequence
<220> FEATURE:
<223> OTHER INFORMATION: Synthetic peptide

<400> SEQUENCE: 5

Ala Arg Val Arg Gly Tyr Ala Met Asp Ala
1               5                   10

<210> SEQ ID NO 6
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 6

Asp Ile Val Leu Thr Gln Ser Pro Ala Thr Leu Ser Val Thr Pro Gly
1               5                   10                  15

Glu Ser Val Ser Leu Ser Cys Arg Ala Ser Gln Asp Ile Ser Thr Ser
            20                  25                  30

Ile His Trp Tyr Gln Gln Lys Ser Asn Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Gly Gly Ser Gly Thr Asp Phe Thr Leu Thr Ile Asn Arg Val Glu Ser
65                  70                  75                  80

Glu Asp Phe Ser Val Tyr Tyr Cys Gln Gln Ser Tyr Ser Leu Pro Val
                85                  90                  95

Thr Phe Gly Ser Gly Thr Lys Leu Glu Leu Lys Arg
            100                 105

<210> SEQ ID NO 7
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 7
gacattgtgc tcacccagtc tccagccacc ctgtctgtga ctccaggaga gagtgtgagt      60
ctctcctgca gggccagtca ggatattagc actagcattc attggtatca gcaaaaatca     120
aatgagtctc caaggcttct catcaagtat gcttcccagt ccatctctgg aatcccctcc     180
aggttcagtg gaggtggatc aggacagat ttcactctca ctatcaacag agtcgaatct     240
gaagattttt cagtttatta ctgtcaacag agttacagct tgcccgtcac gttcggatct     300
gggaccaagc tggaactgaa acgg                                              324

<210> SEQ ID NO 8
<211> LENGTH: 6
<212> TYPE: PRT
<213> ORGANISM: Artificial sequence
<220> FEATURE:
<223> OTHER INFORMATION: Synthetic peptide

<400> SEQUENCE: 8

Gln Asp Ile Ser Thr Ser
1               5

<210> SEQ ID NO 9
<211> LENGTH: 3
<212> TYPE: PRT
<213> ORGANISM: Artificial sequence
<220> FEATURE:
<223> OTHER INFORMATION: Synthetic peptide

<400> SEQUENCE: 9

Tyr Ala Ser
1

<210> SEQ ID NO 10
<211> LENGTH: 9
<212> TYPE: PRT
<213> ORGANISM: Artificial sequence
<220> FEATURE:
<223> OTHER INFORMATION: Synthetic peptide

<400> SEQUENCE: 10

Gln Gln Ser Tyr Ser Leu Pro Val Thr
1               5

<210> SEQ ID NO 11
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 11

Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Ser Asn
            20                  25                  30

Phe Met His Trp Ile Lys Gln Gln Pro Gly Asn Gly Leu Glu Trp Ile
        35                  40                  45

Gly Trp Ile Tyr Pro Gly Asp Gly Asp Thr Asp Tyr Asn Gln Lys Phe
    50                  55                  60

Ile Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ser Arg Ser Asn Ser Gly Tyr Asn Trp Phe Ala Tyr Trp Gly Gln Gly
            100                 105                 110

Thr Leu Val Thr Val Ser Ser
        115

<210> SEQ ID NO 12
<211> LENGTH: 357

<212> TYPE: DNA
<213> ORGANISM: Artificial sequence
<220> FEATURE:
<223> OTHER INFORMATION: Synthetic oligonucleotide

<400> SEQUENCE: 12

```
caggttcagc tgcagcagtc tggggctgaa ctggtgaagc ctgggtcctc agtgaaaatt      60
tcctgcaagg cttctggcta caccttcacc agtaacttta tgcactggat aaaacagcag     120
cctggaaatg gccttgagtg gattgggtgg atttatcctg agatggtga tacagattac      180
aatcaaaagt tcattgggaa ggcaacactc actgcagaca atcctccag cacagcctat      240
atgcagctca gcagcctgac atctgaggac tctgcagtct atttctgttc aagatcgaat     300
tcgggataca attggtttgc ttactggggc caaggcactc tggtcaccgt ctcctca        357
```

<210> SEQ ID NO 13
<211> LENGTH: 8
<212> TYPE: PRT
<213> ORGANISM: Artificial sequence
<220> FEATURE:
<223> OTHER INFORMATION: Synthetic peptide

<400> SEQUENCE: 13

Gly Tyr Thr Phe Thr Ser Asn Phe
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic peptide

<400> SEQUENCE: 14

Ile Tyr Pro Gly Asp Gly Asp Thr
1               5

<210> SEQ ID NO 15
<211> LENGTH: 12
<212> TYPE: PRT
<213> ORGANISM: Artificial sequence
<220> FEATURE:
<223> OTHER INFORMATION: Synthetic peptide

<400> SEQUENCE: 15

Ser Arg Ser Asn Ser Gly Tyr Asn Trp Phe Ala Tyr
1               5                   10

<210> SEQ ID NO 16
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 16

Asp Ile Val Leu Thr Gln Ser Pro Pro Val Leu Ser Ala Ser Val Gly
1               5                   10                  15

Asp Arg Val Thr Leu Ser Cys Lys Ala Ser Gln Asn Ile Asn Lys Asn
            20                  25                  30

Leu Asp Trp Tyr Gln Gln Lys His Gly Glu Ala Pro Lys Leu Leu Ile
        35                  40                  45

Tyr Tyr Thr Asn Asn Leu Gln Thr Gly Ile Pro Ser Arg Phe Ser Gly
    50                  55                  60

```
Ser Gly Ser Gly Thr Asp Tyr Thr Leu Thr Ile Arg Ser Leu Gln Pro
 65                  70                  75                  80

Glu Asp Val Ala Thr Tyr Tyr Cys Tyr Gln Tyr Arg Thr Gly Trp Thr
                 85                  90                  95

Phe Gly Gly Gly Thr Lys Leu Glu Leu Lys Arg
            100                 105

<210> SEQ ID NO 17
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 17
gacattgtgc tcacccagtc tcctccagtc ctgtctgcat ctgtgggaga cagagtcact     60
ctcagctgca aagcaagtca gaatattaat aagaacttag actggtatca acaaaagcat    120
ggagaagctc caaaactcct gatatattat acaaacaatt tgcaaacggg tatcccatca    180
aggttcagtg gcagtggatc tggtacagat tacacactca ccatcagaag cctgcagcct    240
gaggatgttg ccacatatta ctgctatcag tatagaactg gtggaccttc ggtggaggc    300 accaagctgg agttgaaacg g                                              321

<210> SEQ ID NO 18
<211> LENGTH: 6
<212> TYPE: PRT
<213> ORGANISM: Artificial sequence
<220> FEATURE:
<223> OTHER INFORMATION: Synthetic peptide

<400> SEQUENCE: 18

Gln Asn Ile Asn Lys Asn
 1               5

<210> SEQ ID NO 19
<211> LENGTH: 3
<212> TYPE: PRT
<213> ORGANISM: Artificial sequence
<220> FEATURE:
<223> OTHER INFORMATION: Synthetic peptide

<400> SEQUENCE: 19

Tyr Thr Asn
 1

<210> SEQ ID NO 20
<211> LENGTH: 8
<212> TYPE: PRT
<213> ORGANISM: Artificial sequence
<220> FEATURE:
<223> OTHER INFORMATION: Synthetic peptide

<400> SEQUENCE: 20

Tyr Gln Tyr Arg Thr Gly Trp Thr
 1               5
```

LGR4 SPECIFIC MONOCLONAL ANTIBODIES AND METHODS OF THEIR USE

This application is a national phase application under 35 U.S.C. § 371 of International Application No. PCT/US2016/065788, filed Dec. 9, 2016, which claims the benefit of U.S. Provisional Patent Application No. 62/267,409, filed Dec. 15, 2015, the entirety of each of which is incorporated herein by reference.

This invention was made with government support under Grant No. GM102485 awarded by the National Institutes of Health. The government has certain rights in the invention.

BACKGROUND OF THE INVENTION

1. Field of the Invention

The present invention relates generally to the field of cancer biology. More particularly, it concerns LGR4 targeting monoclonal antibodies for the treatment and detection of cancer.

2. Description of Related Art

The leucine-rich repeat-containing G-protein coupled receptor 4 (LGR4), also called G-protein coupled receptor 48 (GPR48), consists of a large extracellular domain (ECD) with 17 leucine-rich repeats and a seven transmembrane (7TM) domain typical of the rhodopsin family of G protein-coupled receptors. It has been demonstrated that LGR4, along with its closely related homologs LGR5 and LGR6, function as receptors of the R-spondin group of stem cell factors to potentiate Wnt signaling (8-10). This function of RSPO-LGR4 signaling is mediated by the inhibition of two E3 ubiquitin ligases (RNF43 and ZNRF3) of Wnt receptors and the recruitment of IQGAP1 to coordinate LRP6 phosphorylation as well as actin dynamics.

As a receptor for R-spondins, LGR4 potentiates the canonical Wnt signaling pathway and is involved in the formation of various organs. Upon binding to R-spondins (RSPO1, RSPO2, RSPO3 or RSPO4), LGR4 associates with phosphorylated LRP6 and frizzled receptors that are activated by extracellular Wnt receptors, triggering the canonical Wnt signaling pathway to increase expression of target genes. In contrast to classical G-protein coupled receptors, LGR4 does not activate heterotrimeric G-proteins to transduce the signal. LGR4 activation of the Wnt signaling pathway is required for the development of various organs, including liver, kidney, intestine, bone, reproductive tract and eye. LGR4 is also required during spermatogenesis to activate the Wnt signaling pathway in peritubular myoid cells and for the maintenance of intestinal stem cells and Paneth cell differentiation in postnatal intestinal crypts. LGR4 also acts as a regulator of bone formation and remodeling and is involved in kidney development. LGR4 is also involved in the development of the anterior segment of the eye; required during erythropoiesis; and also acts as a negative regulator of innate immunity by inhibiting TLR2/TLR4 associated pattern-recognition and proinflammatory cytokine production. LGR4 is also believed to play an important role in regulating the circadian rhythms of plasma lipids, partially through regulating the rhythmic expression of MTTP. The complex interactions of LGR4 receptors and ligands provide a great potential for significant therapeutic intervention.

SUMMARY OF THE INVENTION

Described herein are LGR4 monoclonal antibodies that potently block LGR4 signaling and inhibit cancer cell proliferation. Thus, in a first embodiment, there is provided an isolated or recombinant monoclonal antibody that specifically binds to a LGR4. In certain aspects, an antibody that competes for the binding of a LGR4 with the 8D2 or 3G6 monoclonal antibody is provided. In certain aspects, the antibody may comprise all or part of the heavy chain variable region and/or light chain variable region of the 8D2 or 3G6 monoclonal antibodies. In a further aspect, the antibody may comprise an amino acid sequence that corresponds to a first, second, and/or third complementarity determining region (CDR) from the light variable and/or heavy variable chain of the 8D2 or 3G6 monoclonal antibodies of the present embodiments.

In certain aspects, the isolated antibody comprises CDR sequences at least 80%, 90%, or 95% identical to the CDR regions of the 8D2 or 3G6 heavy and light chain amino acid sequences. In further aspects, an antibody comprises CDR regions identical to the 8D2 or 3G6 CDR regions, except for one or two amino acid substitutions, deletions, or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of a 8D2 or 3G6 monoclonal antibody. Thus, in some specific aspects, an antibody of the embodiments comprises (a) a first $V_H$ CDR at least 80% identical to $V_H$ CDR1 of 8D2 (SEQ ID NO: 3) or 3G6 (SEQ ID NO: 13); (b) a second $V_H$ CDR at least 80% identical to $V_H$ CDR2 of 8D2 (SEQ ID NO: 4) or 3G6 (SEQ ID NO: 14); (c) a third $V_H$ CDR at least 80% identical to $V_H$ CDR3 of 8D2 (SEQ ID NO: 5) or 3G6 (SEQ ID NO: 15); (d) a first $V_L$ CDR at least 80% identical to $V_L$ CDR1 of 8D2 (SEQ ID NO: 8) or 3G6 (SEQ ID NO: 18); (e) a second $V_L$ CDR at least 80% identical to $V_L$ CDR2 of 8D2 (SEQ ID NO: 9) or 3G6 (SEQ ID NO: 19); and (f) a third $V_L$ CDR at least 80% identical to $V_L$ CDR3 of 8D2 (SEQ ID NO: 10) or 3G6 (SEQ ID NO: 20). In certain aspects, such an antibody is a humanized or de-immunized antibody comprising the foregoing CDRs on a human IgGs (e.g., IgG1, IgG2, IgG4, or a genetically modified IgG) backbone.

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody 8D2, which are represented by SEQ ID NOs: 3, 4, 5, 8, 9, and 10, respectively. In one aspect, the isolated antibody comprises CDR sequences that are identical to the CDR sequences of monoclonal antibody 8D2.

In another aspect, the isolated antibody comprises a $V_H$ domain at least about 80% identical to the $V_H$ domain of 8D2 (SEQ ID NO: 1) or the humanized $V_H$ domain of 8D2 mAB; and a $V_L$ domain at least about 80% identical to the $V_L$ domain of 8D2 (SEQ ID NO: 6) or the humanized $V_L$ domain of 8D2 mAB. For example, the antibody can comprise a $V_H$ domain at least 95% identical to the $V_H$ domain of the humanized 8D2 mAB and a $V_L$ domain at least 95% identical to the $V_L$ domain of the humanized 8D2 mAB. Thus, in some aspects, an antibody comprises a $V_H$ domain identical to the $V_H$ domain of humanized 8D2 mAB and a $V_L$ domain identical to the $V_L$ domain of the humanized 8D2 mAB. In a specific example, the isolated antibody can comprise $V_H$ and $V_L$ domains identical to those of monoclonal antibody 8D2.

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody 3G6, which are represented by SEQ ID NOs: 13, 14, 15, 18, 19, and 20, respectively. In one aspect, the isolated antibody comprises CDR sequences that are identical to the CDR sequences of monoclonal antibody 3 G6.

In another aspect, the isolated antibody comprises a $V_H$ domain at least about 80% identical to the $V_H$ domain of 3G6 (SEQ ID NO: 11) or the humanized 3G6 mAB; and a $V_L$ domain at least about 80% identical to the $V_L$ domain of 3G6 (SEQ ID NO: 16) or the humanized 3G6 mAB. Thus, in some aspects, the antibody comprises a $V_H$ domain at least 95% identical to the $V_H$ domain of the humanized 3G6 mAB and a $V_L$ domain at least 95% identical to the $V_L$ domain of the humanized 3G6 mAB. For instance the antibody can comprise a $V_H$ domain identical to the $V_H$ domain of the humanized 3G6 mAB and a $V_L$ domain identical to the $V_L$ domain of the humanized 3G6 mAB. In a specific example, the isolated antibody can comprise $V_H$ and $V_L$ domains identical to those of monoclonal antibody 3G6.

In some aspects, an antibody of the embodiments may be an IgG (e.g., IgG1, IgG2, IgG3 or IgG4), IgM, IgA, genetically modified IgG isotype, or an antigen binding fragment thereof. The antibody may be a Fab', a F(ab')2 a F(ab')3, a monovalent scFv, a bivalent scFv, a bispecific or a single domain antibody. The antibody may be a human, humanized, or de-immunized antibody. In a further aspect, the isolated antibody is the 8D2 or 3G6 antibody.

In some aspects, the antibody may be conjugated to an imaging agent, a chemotherapeutic agent, a toxin, or a radionuclide.

In one embodiment, there is provided a recombinant polypeptide comprising an antibody $V_H$ domain comprising CDRs 1-3 of the $V_H$ domain of 8D2 (SEQ ID NOs: 3, 4, and 5) or CDRs 1-3 of the $V_H$ domain of 3G6 (SEQ ID NOs: 13, 14, and 15). In another embodiment, there is provided a recombinant polypeptide comprising an antibody $V_L$ domain comprising CDRs 1-3 of the $V_L$ domain of 8D2 (SEQ ID NOs: 8, 9, and 10) or 3G6 (SEQ ID NOs: 18, 19, and 20).

In some embodiments, there is provided an isolated polynucleotide molecule comprising nucleic acid sequence encoding an antibody or a polypeptide comprising an antibody $V_H$ or $V_L$ domain disclosed herein.

In further embodiments, a host cell is provided that produces a monoclonal antibody or recombinant polypeptide of the embodiments. In some aspects, the host cell is a mammalian cell, a yeast cell, a bacterial cell, a ciliate cell, or an insect cell. In certain aspects, the host cell is a hybridoma cell.

In still further embodiments, there is provided a method of manufacturing an antibody of the present invention comprising expressing one or more polynucleotide molecule(s) encoding a $V_L$ or $V_H$ chain of an antibody disclosed herein in a cell and purifying the antibody from the cell.

In additional embodiments, there are pharmaceutical compositions comprising an antibody or antibody fragment as discussed herein. Such a composition further comprises a pharmaceutically acceptable carrier and may or may not contain additional active ingredients.

In embodiments of the present invention, there is provided a method for treating a subject having a cancer comprising administering an effective amount of an antibody disclosed herein. In certain aspects, the antibody is a monoclonal antibody of the embodiments herein, such as the 8D2 or 3G6 antibody or a recombinant polypeptide comprising antibody segment derived therefrom.

In certain aspects, the cancer may be a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer.

In one aspect, the antibody may be administered systemically. In additional aspects, the antibody may be administered intravenously, intradermally, intratumorally, intramuscularly, intraperitoneally, subcutaneously, or locally. The method may further comprise administering at least a second anticancer therapy to the subject. Examples of the second anticancer therapy include, but are not limited to, surgical therapy, chemotherapy, radiation therapy, cryotherapy, hormonal therapy, immunotherapy, or cytokine therapy.

In further aspects, the method may further comprise administering a composition of the present invention more than one time to the subject, such as, for example, 1, 2, 3, 4, 5, 6, 7, 8, 9, 10, 15, 20 or more times.

In another embodiment, there is provided a method for detecting a cancer in a subject comprising testing for the presence of elevated LGR4 relative to a control in a sample from the subject, wherein the testing comprises contacting the sample with an antibody disclosed herein. For example, the method may be an in vitro or in vivo method.

Certain embodiments are directed to an antibody or recombinant polypeptide composition comprising an isolated and/or recombinant antibody or polypeptide that specifically binds LGR4. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein or a combination of such sequences.

In still further aspects, an antibody or polypeptide of the embodiments comprises one or more amino acid segments of the any of the amino acid sequences disclosed herein. For example, the antibody or polypeptide can comprise 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 amino acids in length, including all values and ranges there between, that are at least 80, 85, 90, 95, 96, 97, 98, 99, or 100% identical to any of the amino acid sequences disclosed herein. In certain aspects the amino segment(s) are selected from one of the amino acid sequences of a LGR4-binding antibody as provided in Table 1.

In still further aspects, an antibody or polypeptide of the embodiments comprises an amino acid segment of the any of the amino acid sequences disclosed herein, wherein the segment begins at amino acid position 1, 2, 3, 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in any sequence provided herein and ends at amino acid position 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in the same provided sequence. In certain aspects the amino segment(s), or portions thereof, are selected from one of the amino acid sequences of a LGR4-binding antibody as provided in Table 1.

In yet further aspects, an antibody or polypeptide of the embodiments comprises an amino acid segment that is at least 80, 85, 90, 95, 96, 97, 98, 99, or 100% identical (or any range derivable therein) to a V, VJ, VDJ, D, DJ, J or CDR domain of a LGR4-binding antibody (as provided in Table 1). For example, a polypeptide may comprise 1, 2 or 3 amino acid segment that are at least 80, 85, 90, 95, 96, 97, 98, 99, or 100% identical (or any range derivable therein) to CDRs 1, 2, and/or 3 a LGR4-binding antibody as provided in Table 1.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

cells after 4 days of antibody treatment. Cell viability was determined using the CelltiterGlo™ assay. Error bars are S.E.M. (n=3).

Figure 6:
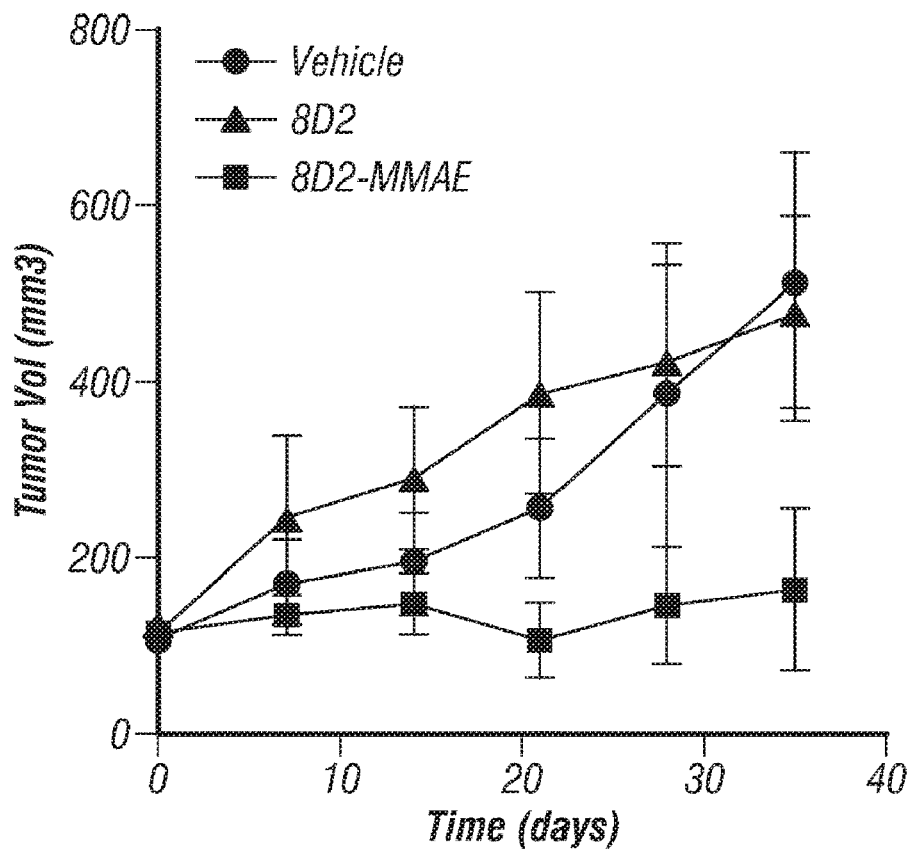

FIG. 6. LGR4 ADC inhibits the growth of xenograft tumors in vivo. OVCAR3 cells were implanted subcutaneously into nude mice. The animals were dosed with vehicle or the indicated substances every 10 days when tumors reached an average size of ~100 mm3.

Figure 7:
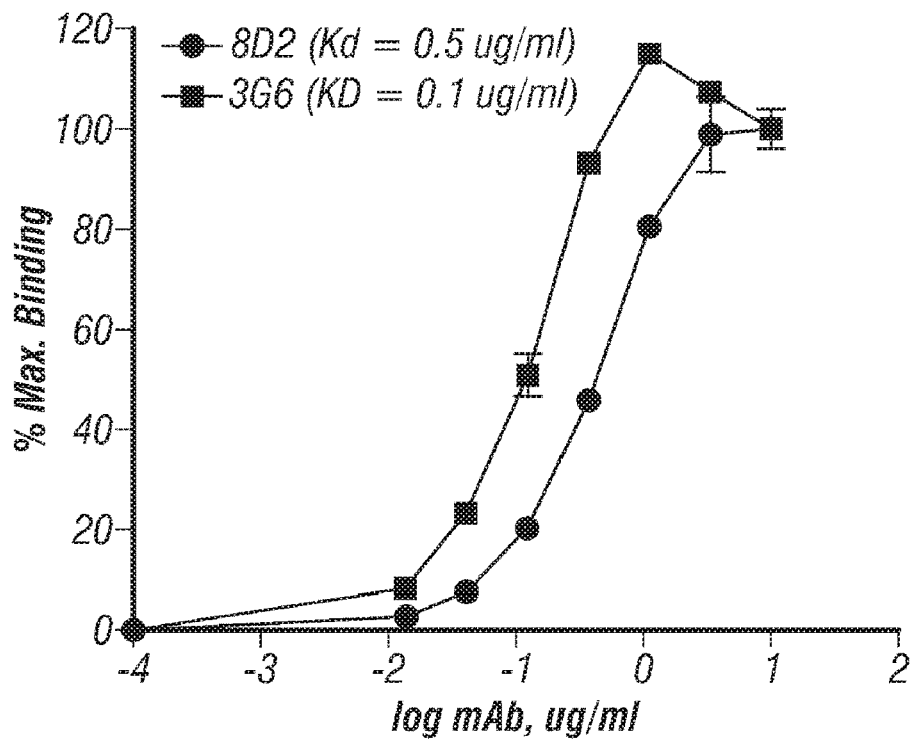

FIG. 7. Binding of anti-LGR4 mAbs 8D2 and 3G6 to LGR4. Serial dilutions of the purified 8D2 and 3G6 were incubated with HEK293 cells overexpressing LGR4, washed, fixed, and incubated with Alexa-488-labeled anti-rat IgG and then washed. Binding was based on amount of fluorescence retained by the cells.

Figure 8:
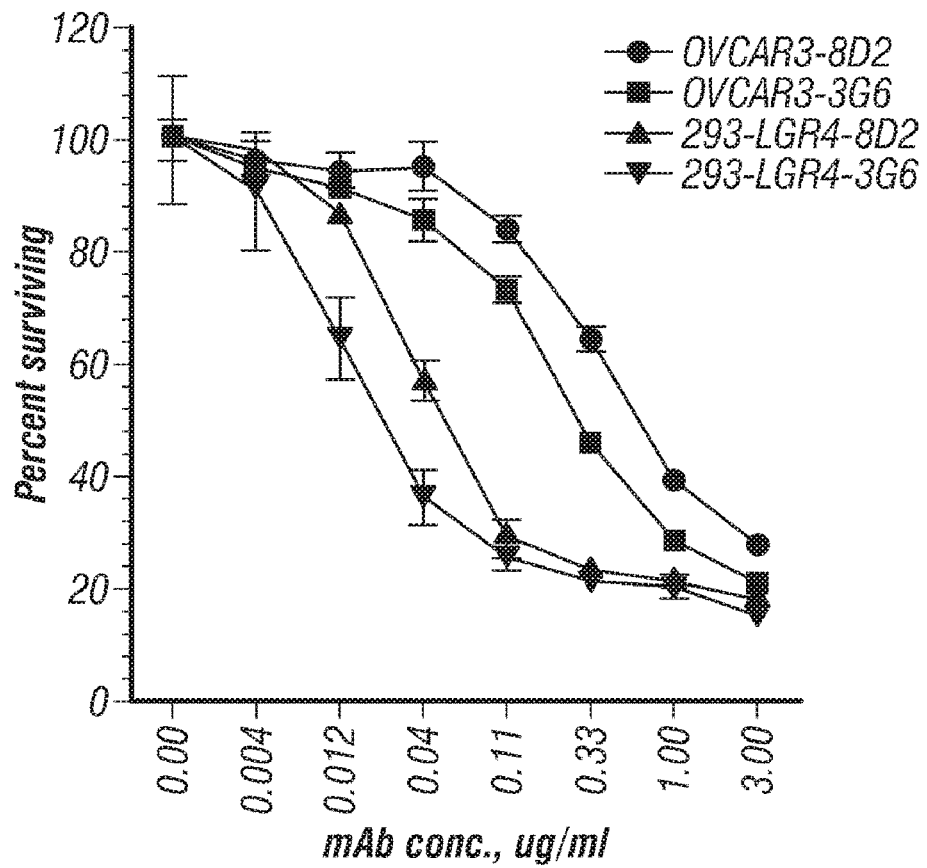

FIG. 8. Comparison of cytostatic effect of 3G6 and 8D2 in the presence of MMAF-conjugated anti-rat IgG. Serial dilution of 8D2 or 3G6 mixed with MMAF-conjugated anti-rat IgG (ratio=1:2) were incubated with the ovarian cancer cell line OVCAR3 cells or HEK293 cells overexpression LGR4 for 4 days. Cell viability was determined using the cell titer glo assays.

DESCRIPTION OF ILLUSTRATIVE EMBODIMENTS

I. Antibodies of the Embodiments

In certain embodiments, an antibody or a fragment thereof that binds to at least a portion of LGR4 protein and inhibits LGR4 signaling and cancer cell proliferation are contemplated. As used herein, the term "antibody" is intended to refer broadly to any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-LGR4 antibody is a monoclonal antibody or a humanized antibody.

Thus, by known means and as described herein, polyclonal or monoclonal antibodies, antibody fragments, and binding domains and CDRs (including engineered forms of any of the foregoing) may be created that are specific to LGR4 protein, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as a LGR4 extracellular domain (ECD) protein, in order to produce antibodies specific for LGR4 protein. The ECD may have 17 leucine-rich repeats and a seven transmembrane (7TM) domain typical of the rhodopsin family of G protein-coupled receptors. GenBank entries include: AF346711, AF346709, AF346710 (Genomic DNA), AAK31153.1 (Translation), BC033039, AAH33039.1 (mRNA and translation) and UniProtKB-Q9BXB1 (LGR4 Human). The LGR4 extracellular domain proteins may include amino acids 25-544, 597-620, 683-703, and 778-783 of UniProtKB Accession No. Q9BXB1. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (mAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a LGR4 antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

Plasma B cells (CD45+CD5-CD19+) may be isolated from freshly prepared rabbit peripheral blood mononuclear cells of immunized rabbits and further selected for LGR4 binding cells. After enrichment of antibody producing B cells, total RNA may be isolated and cDNA synthesized. DNA sequences of antibody variable regions from both heavy chains and light chains may be amplified, constructed into a phage display Fab expression vector, and transformed into *E. coli*. LGR4 specific binding Fab may be selected out through multiple rounds enrichment panning and sequenced. Selected LGR4 binding hits may be expressed as full length IgG in rabbit and rabbit/human chimeric forms using a mammalian expression vector system in human embryonic kidney (HEK293) cells (Invitrogen) and purified using a protein G resin with a fast protein liquid chromatography (FPLC) separation unit.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in: Marks (1992); Stemmer (1994); Gram et al. (1992); Barbas et al. (1994); and Schier et al. (1996).

It is fully expected that antibodies to LGR4 will have the ability to neutralize or counteract the effects of LGR4 regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds LGR4.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Figure 1:
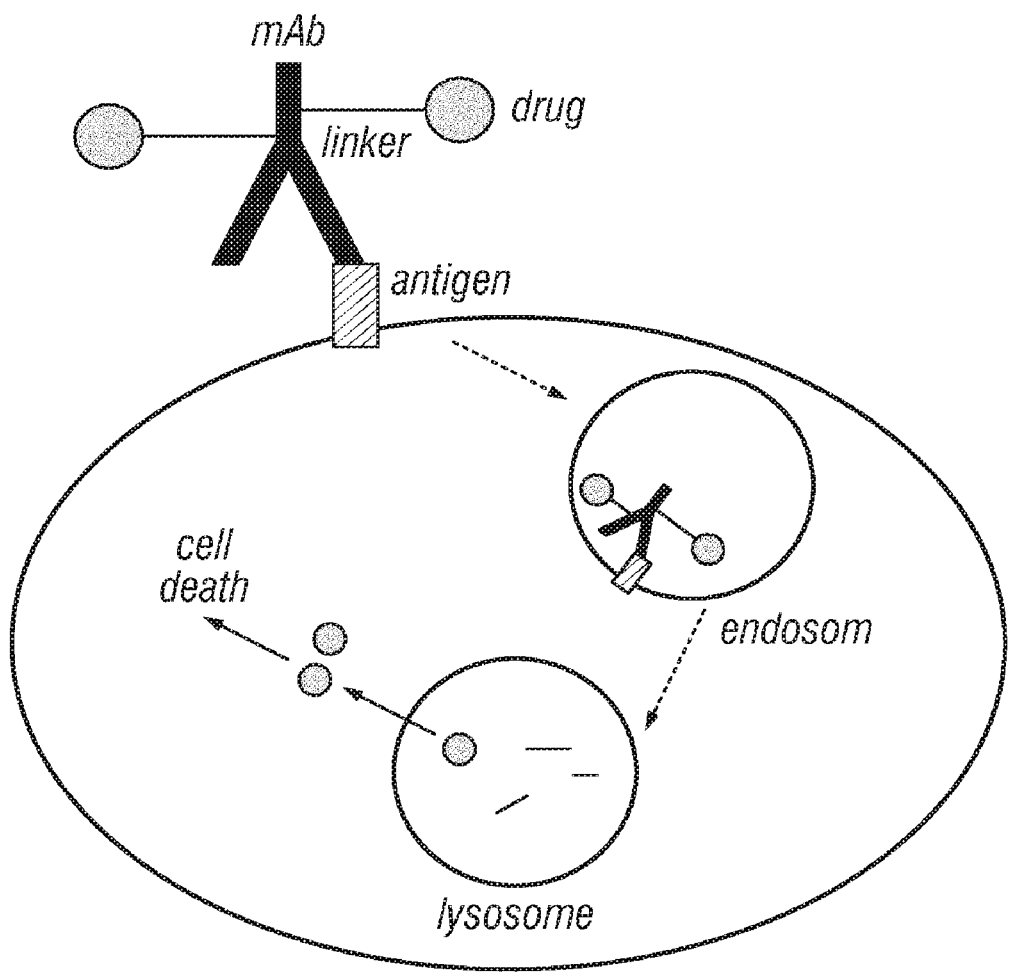
FIG. 1. A schematic diagram illustrating the working principles of ADC (antibody-drug conjugate). Upon binding to its target antigen, the mAb-antigen complex is internalized into endosomes which is then fused with lysosomes where the mAb is degraded and the drug is released.

Antibody-drug conjugates have emerged as a breakthrough approach to the development of cancer therapeutics. Cancer is one of the leading causes of deaths in the world. Antibody-drug conjugates (ADCs) comprise monoclonal antibodies (mAbs) that are covalently linked to cell-killing drugs (see, e.g., FIG. 1). Thus, embodiments provide antibodies and antibody-like molecules against LGR4, polypeptides and peptides that are linked to at least one agent to form an antibody conjugate or payload. In some aspects, this approach combines the high specificity of mAbs against their antigen targets with highly potent cytotoxic drugs, resulting in "armed" mAbs that deliver the payload (drug) to tumor cells with enriched levels of the antigen (Carter et al., 2008; Teicher 2014; Leal et al., 2014). Targeted delivery of the drug also minimizes its exposure in normal tissues, resulting in decreased toxicity and improved therapeutic index. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

In light of the noted oncogenic association of LGR4 and its broad expression at high levels in many major types of epithelial tumor cells and this added identification of spontaneous internalization, LGR4 presented itself as an excellent target of ADC-based drug development for the treatment of LGR4-high tumors. Indeed, the anti-LGR4 monoclonal antibodies disclosed herein demonstrate that an auristatin-conjugated LGR4 ADC had a strong cytotoxic effect in vitro on multiple LGR4-high cancer cell lines. As exemplified below, novel anti-LGR4 monoclonal antibodies with improved properties can be used to generate LGR4 ADC displaying strong cytotoxic effects on multiple LGR4-expressing human cancer cells, both in vitro and in vivo.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

II. Treatment of Diseases

Certain aspects of the present embodiments can be used to prevent or treat a disease or disorder associated with LGR4 signaling. Signaling of LGR4 may be reduced by any suitable drugs to prevent cancer cell proliferation. Preferably, such substances would be an anti-LGR4 antibody.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that inhibits the LGR4 signaling.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

A. Pharmaceutical Preparations

Where clinical application of a therapeutic composition containing an inhibitory antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

B. Combination Treatments

In certain embodiments, the compositions and methods of the present embodiments involve an antibody or an antibody fragment against LGR4 to inhibit its activity in cancer cell proliferation, in combination with a second or additional therapy. Such therapy can be applied in the treatment of any disease that is associated with LGR4-mediated cell proliferation. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

| | | | | |
|---|---|---|---|---|
| A/B/A | B/A/B | B/B/A | A/A/B | A/B/B |
| B/A/A | A/B/B/B | B/A/B/B | B/B/B/A | B/B/A/B |
| A/A/B/B | A/B/A/B | A/B/B/A | B/B/A/A | B/A/B/A |
| B/A/A/B | A/A/A/B | B/A/A/A | A/B/A/A | A/A/B/A |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

i. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

ii. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

iii. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

iv. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

III. Kits and Diagnostics

In various aspects of the embodiments, a kit is envisioned containing therapeutic agents and/or other therapeutic and delivery agents. In some embodiments, the present embodiments contemplates a kit for preparing and/or administering a therapy of the embodiments. The kit may comprise one or more sealed vials containing any of the pharmaceutical compositions of the present embodiments. The kit may include, for example, at least one LGR4 antibody as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—LGR4 is Highly Upregulated in Many Major Types of Solid Tumors

Figure 2A:
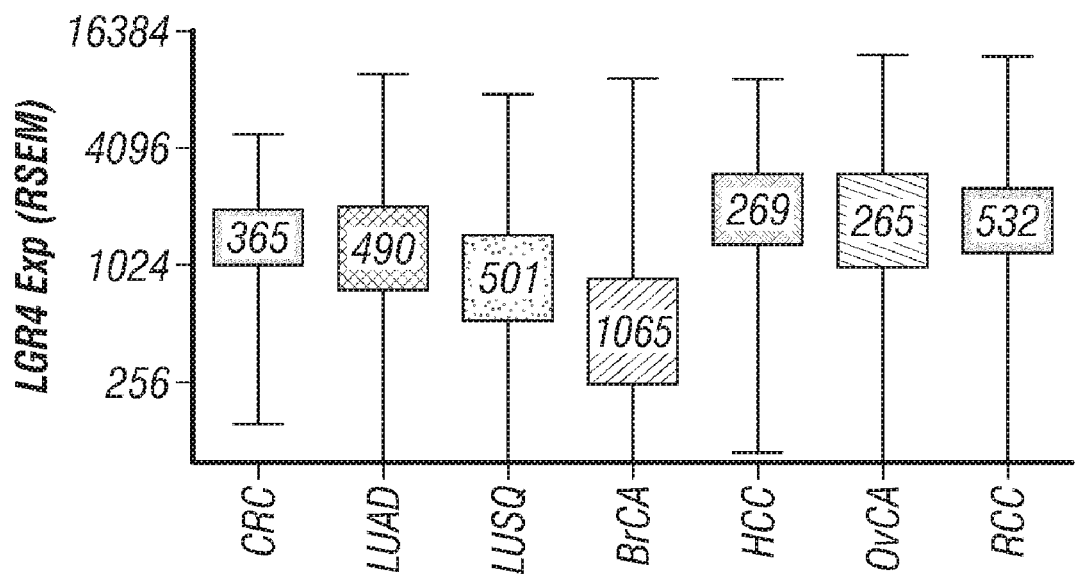
FIGS. 2A-2B. LGR4 is highly expressed in primary tumors and cell lines of major epithelial cancers. 2A: RNA-seq data of LGR4 from TCGA are presented by a box and whiskers plot (top and lower bar are max and min values, respectively. The box represents the 95% confidence range of the mean for each tumor type). 2B: Microarray expression data (normalized) of LGR4 in box and whiskers plot. Numbers in each box represent the number of cases/cell lines with expression data. CRC=colorectal adenocarcinoma; LUAD=lung adenocarcinoma; LUSQ=lung squamous cell carcinoma; BrCa=breast cancer; HCC=hepatocellular carcinoma; OvCA=ovarian cancer; RCC=kidney renal clear cell carcinoma; LuCA, lung cancer; KiCA, kidney cancer. All data were downloaded from the cBioportal website (cbioportal.org).
Figure 2B:
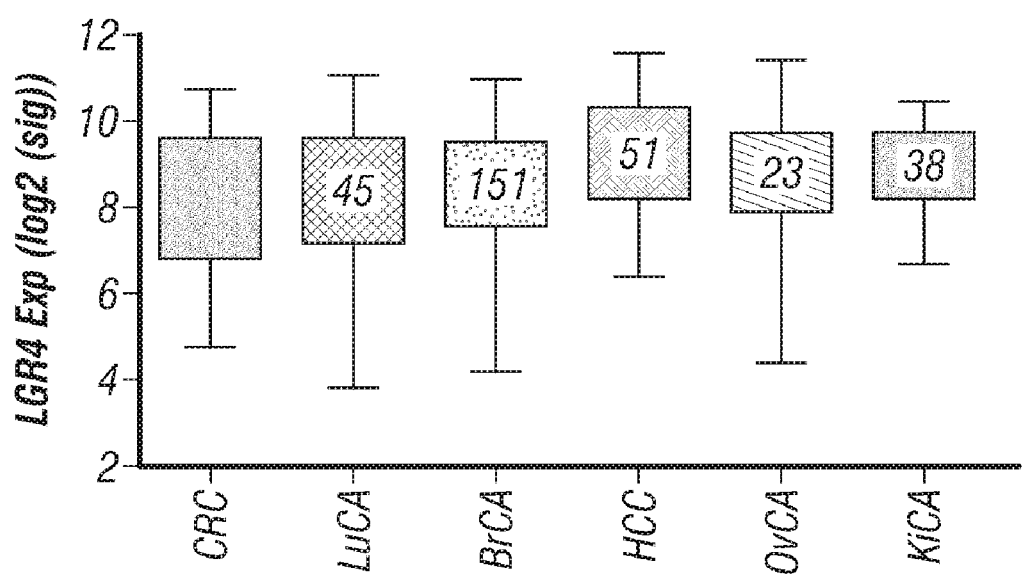

LGR4 is highly upregulated in colorectal cancer (CRC) and non-small cell lung cancer (NSCLC). Recurrent, gain-of-expression gene fusions of RSPO2 (to EIF3E) and RSPO3 (PTPRK) occur in a fraction of colorectal and other cancers as a driving mechanism. Recently, the inventors demonstrated that in lung adenocarcinoma (LUAD) gainof-expression of RSPO3 was driven by NRF2 activation instead of gene fusion (Gong, et al., 2014). This aberrant RSPO3-LGR4 signaling promotes tumor aggressiveness. Utilizing the RNA-sequence data provided by The Cancer Genome Atlas (TCGA, cancergenome.nih.gov) for a large number cases across multiple types of solid tumors, the expression of LGR4 across the major types of solid tumors was examined and it was confirmed that the receptor is highly expressed in CRC and NSCLC (FIG. 2A). LGR4 was also found to be expressed at similar or even higher levels in hepatocellular carcinoma (HCC), ovarian serous adenocarcinoma (OvCA), and kidney renal cell carcinoma (RCC) (FIG. 2A). Importantly, expression level of LGR4 is also high across cancer cell lines of the same tumor types (FIG. 2B) based on microarray data of gene expression in the CCLE (Cancer Cell Line Encyclopedia) database (Barretina, et al. 2012), indicating that LGR4 is expressed in cancer cells of primary tumors instead of stromal cells.

Example 2—Anti-LGR4 Monoclonal Antibodies

Figure 3A:
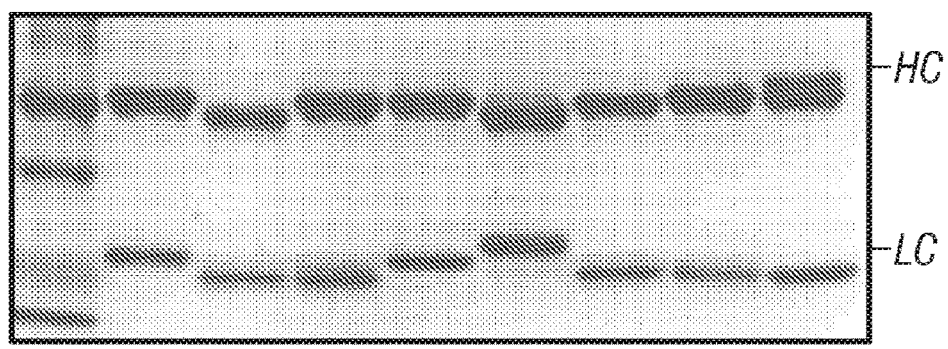
FIGS. 3A-3F. Identification and characterization of anti-LGR4 mAbs. 3A: Eight mAbs were purified to homogeneity. HC, heavy chain; LC, light chain. 3B: Seven purified rat mAbs gave dose-dependent binding to HEK293 cells stably expressing human LGR4. 3C: mAb 8D2 only detected recombinant LGR4 in WB. The lanes are: 1, HEK293, 2, HEK293-LGR4-mouse, 3, HEK293-LGR4-human, 4, breast cancer cell line BT474, 5, HeLa cells. 3D: ICC of 8D2 bound to LGR4 on the cell surface in HEK293 cells stably expressing LGR4. 3E: Binding of 8D2 to lung cancer cell line A549 cells led to its internalization (left panel), which was competed off by conditioned media containing LGR4-ECD (mid-panel) but not by control conditioned media (right panel). 3F: 8D2 (green) and RSPO1-Fc (red) were co-internalized in A549 cells.
Figure 3B:
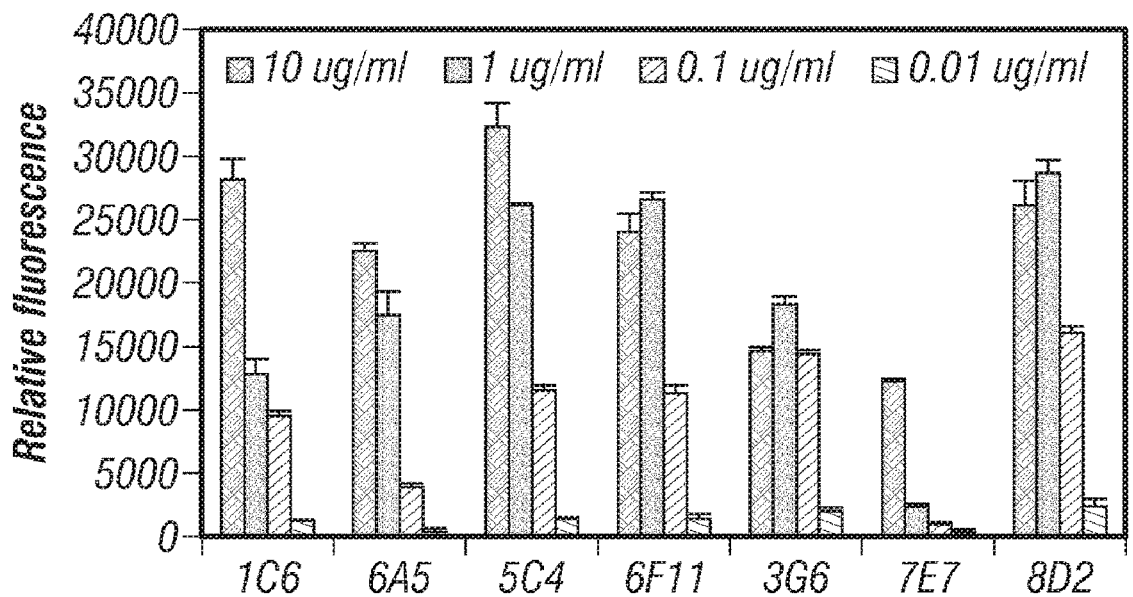
Figure 3C:
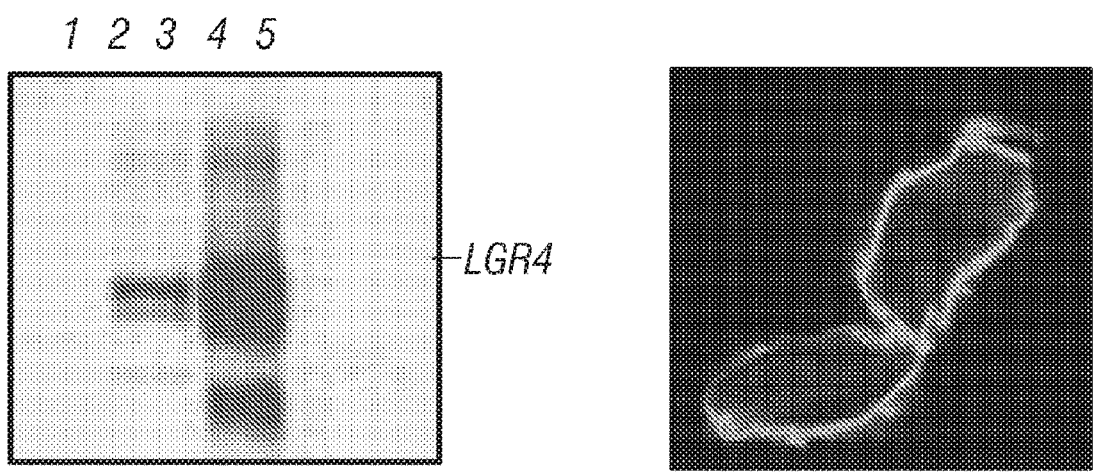
Figure 3D:
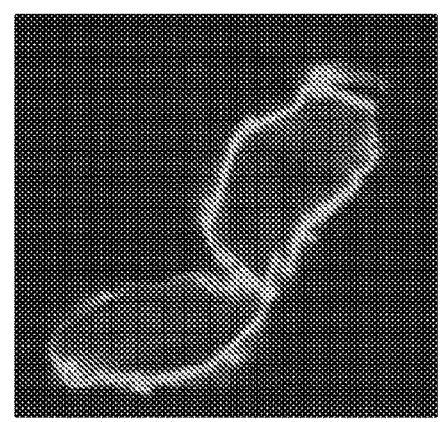
Figure 3E:
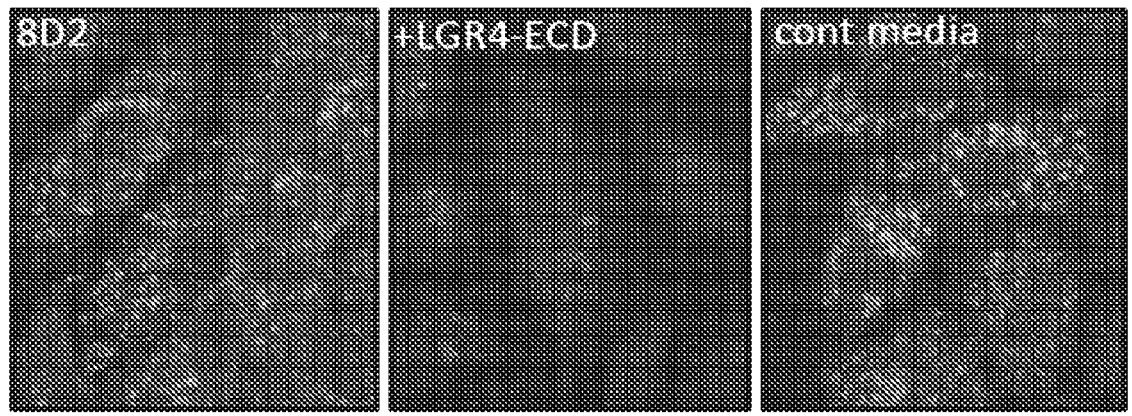
Figure 3F:
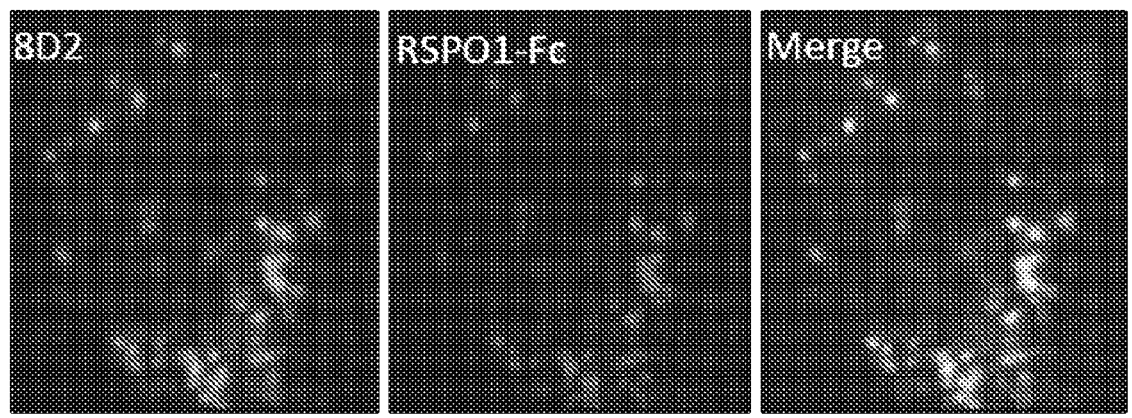

Anti-LGR4 monoclonal antibodies were generated under contract by the company Aldevron/Genovac (Aldevron, Fargo, N. Dak., USA, aldevron.com) using DNA-based immunization of rats with a vector containing full-length human LGR4. After a series of steps from antibody purification to characterization, sixteen (16) clones were identified that produced LGR4-binding monoclonal antibodies. To further characterize the monoclonal antibodies, eight clones with the best apparent binding affinity were scaled up and purified using protein G-based affinity chromatography (FIG. 3A). Analysis of their binding affinity using live HEK293 cells stably expressing human LGR4 revealed that the clone 8D2 was the best with Kd=~0.1 µg/ml (0.7 nM) (FIG. 3B). It also binds native mouse receptor with similar affinity (human and mouse LGR4 are 93% identical in the ECD at the amino acid level). With denatured proteins (Western blots), 8D2 detected recombinant LGR4 of human and mouse (lower affinity) origin at the expected size without non-specific binding (FIG. 3C), and it bound to native LGR4 on the cell surface expressed on HEK293 cells (FIG. 3D). Next, the binding of 8D2 to the lung cancer cell line A549 cells which express high levels of LGR4 endogenously was determined. Incubation of 8D2 with live A549 cells at 37 degrees C. led to its rapid internalization (FIG. 3E, left panel). Importantly, the internalized signal was completely blocked by conditioned media containing LGR4-ECD but not by control conditioned media (FIG. 3E). Furthermore, internalized 8D2 was totally co-localized the LGR4 ligand RSPO1 when 8D2 and RSPO1-Fc were incubated together (FIG. 3F), indicating that 8D2 binds to LGR4 specifically without blocking its ligand binding site. In addition, a specificity cross check analysis showed that none of the 8 monoclonal antibodies bound to LGR5 or LGR6.

Example 3—Internalization of LGR4-mAb-8D2

Figure 4:
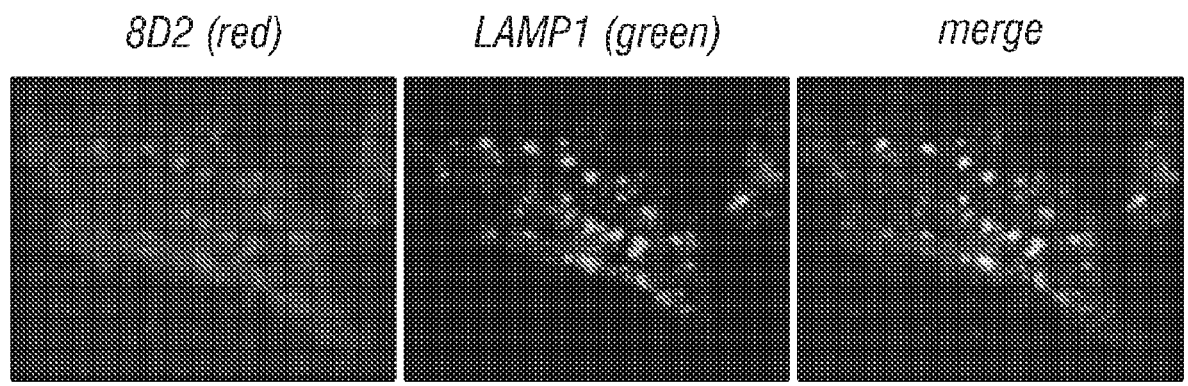
FIG. 4. The LGR4-mAb complex is internalized into the lysosome. 8D2 was incubated with SKOV3 cells for 4 hours, fixed, permeabilized, co-stained with anti-rat (red) and anti-LAMP1 (green) antibodies, and viewed by confocal microscopy.

LGR4-mAb-8D2 complex was co-internalized into lysosome. Current antibody-drug conjugate (ADC) approaches generally require internalization of the antigen-ADC complex into the lysosome where the payload cytotoxin can be released by protease-mediated digestion. Therefore to investigate the potential of LGR4-mAb-8D2 complex for use in ADC, the fate of the mAb 8D2 following incubating with ovarian cancer cell line SKOV3 cells which express high levels of LGR4 (LGR4-high cancer cells) and it was determined that the antibody was completely co-localized with the lysosome marker LAMP1 (FIG. 4), indicating that LGR4 is a suitable target for ADCs that are designed to rely on lysosomal proteases.

Example 4—In Vitro Activity of Anti LGR4-8D2-MMAE Conjugate

Figure 5A:
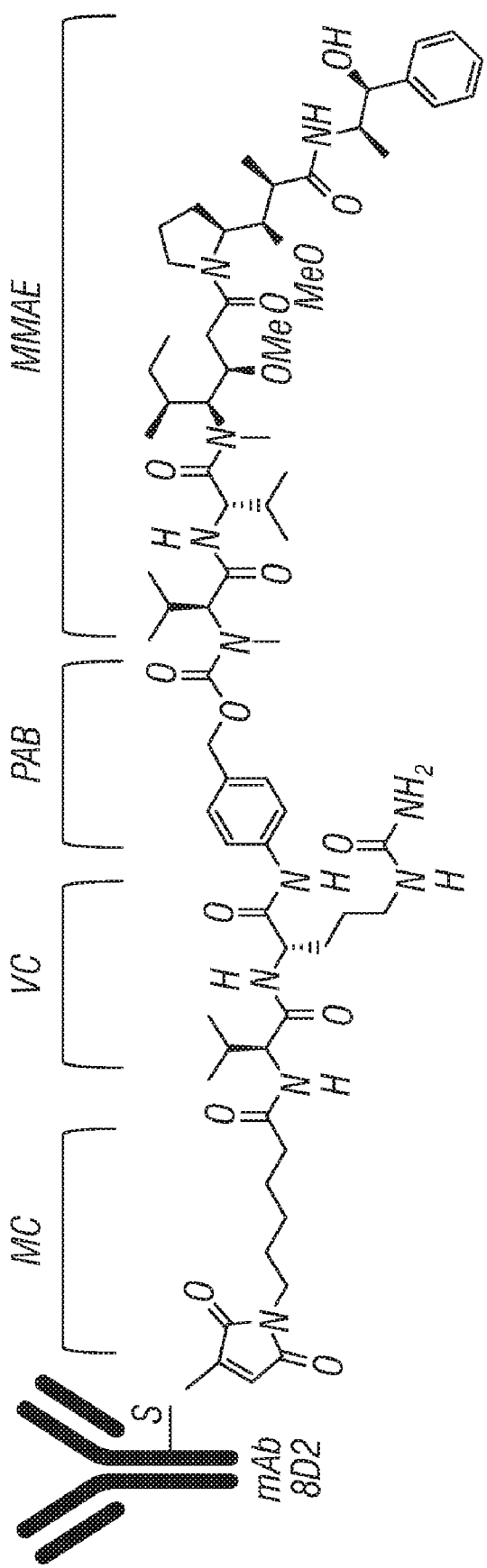
FIGS. 5A-5D. LGR4 mAb ADC showed cytotoxic activity in LGR4-high cancer cell lines. 5A: diagram of the 8D2-MC-VC-PAB-MMAE (8D2-MMAE) ADC. 5B-5D: Dose response curves of 8D2-MMAE and naked 8D2 on the viability of OVCAR3 (B), IGROV1 (C), and SKOV3(D)

LGR4-mAb-8D2 conjugated to auristatin (8D2-MMAE) inhibits the growth of cancer cell lines. To directly demonstrate that LGR4-targeted ADCs can inhibit the growth of LGR4-high cancer cells, the mAb 8D2 was conjugated with the toxin auristatin through a MC-VC-PAB (maleimidocaproyl-valine-citrulline-p-aminobenzyloxycarbonyl) linker in which the valine-citrulline peptide bond is subject to cleavage by proteases in the lysosome (as described in Doronina et al., 2003, and diagramed in FIG. 5A). Auristatin is a highly potent inhibitor of microtubule assembly and is the payload used in the clinically approved drug ADCETRIS® (brentuximab vedotin).

Figure 5B:
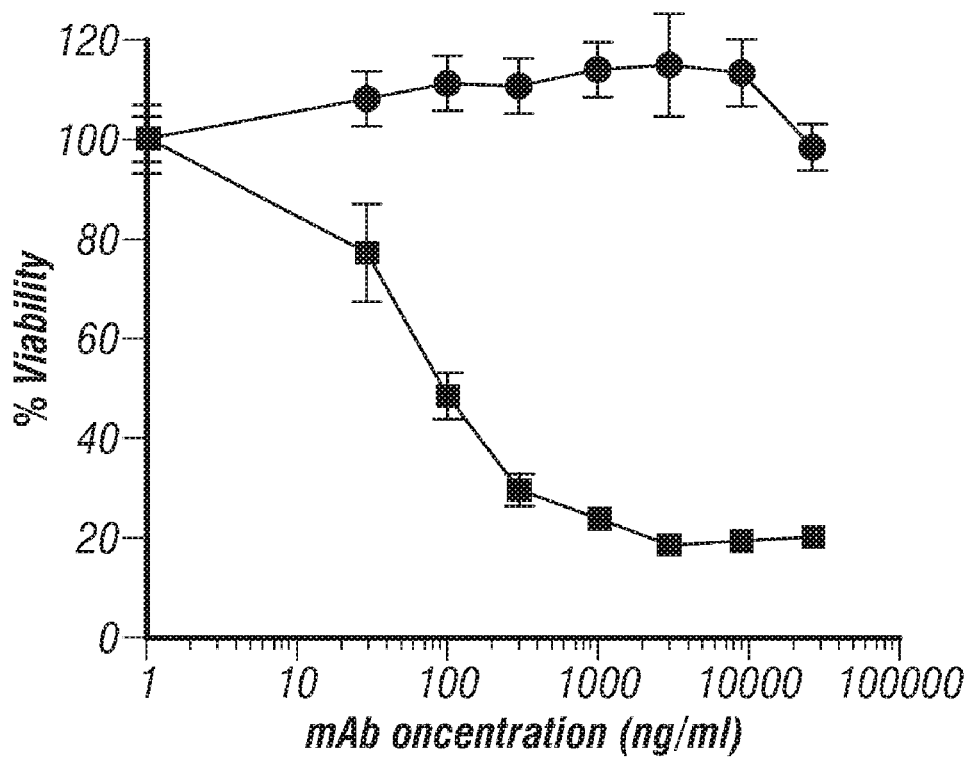
Figure 5C:
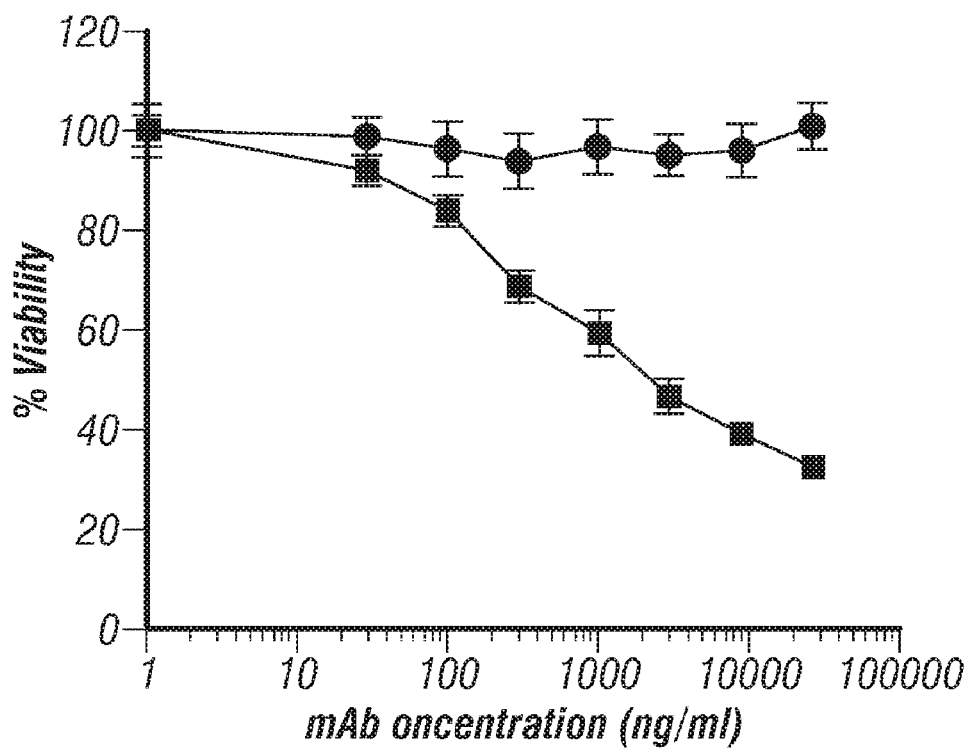
Figure 5D:
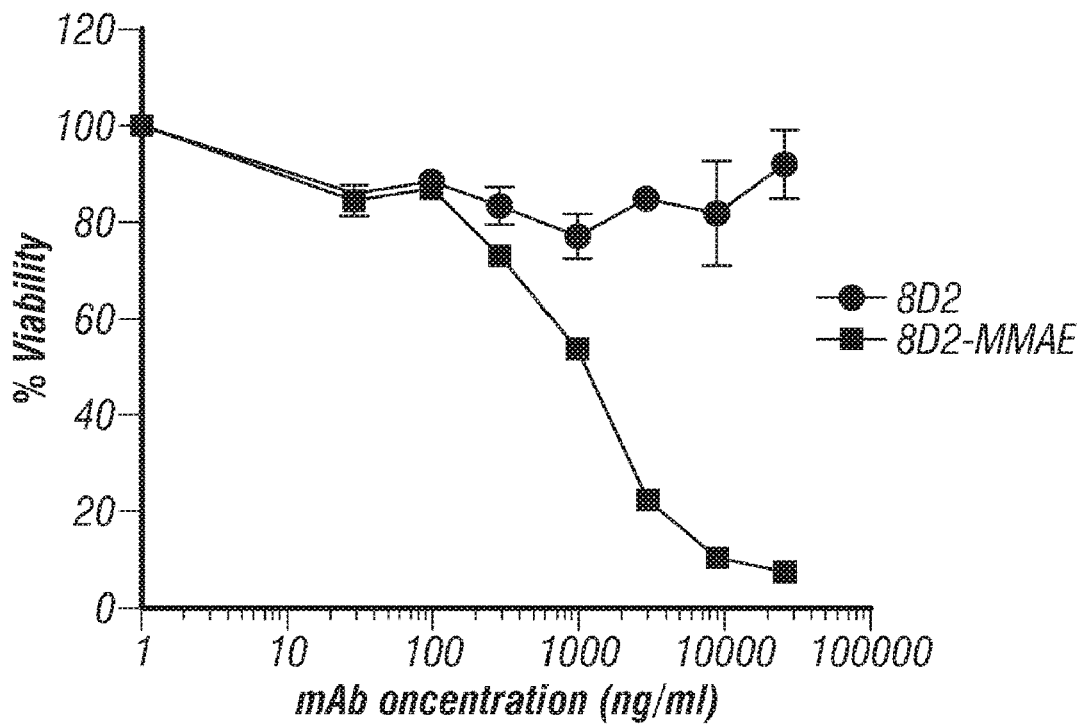

A549 cells were used to confirm the binding affinity of mAb 8D2 was conjugated with auristatin (8D2-MMAE) to LGR4. A panel of cell lines with high levels of LGR4 that are represent the major types of epithelial cancers expressing LGR4 were used to validate that 8D2-MMAE was high toxic to a series of ovarian cancer cell lines (FIGS. 5B-5D).

The IC50 for 8D2-MMAE on the cell lines were: OVCAR3, ~30 ng/ml; IGROV1, ~300 ng/ml; and SKOV3, 2.4 ug/ml (FIG. 5B-D). In contrast, 8D2 antibody that was not coupled to toxin, showed no effect on the growth of these cells (FIGS. 5B-5D). These results strongly suggest that anti-LGR4 ADCs have particular therapeutic potential for the treatment of ovarian cancer.

Example 5—In Vivo Activity of 8D2-MMAE

8D2-MMAE inhibits the growth of OVCAR3 xenograft tumors in vivo. A pilot study was carried out to test if 8D2-MMAE could inhibit the growth of OVCAR3 xenograft tumor in vivo. Tolerability of 8D2-MMAE was first tested in non-tumor bearing mice and it was found that a single dose of the ADC was well tolerated at 10 mg/kg. OVCAR3 cells were implanted subcutaneously into the dorsal flanks of athymic nude mice and when tumors reached an average size of ~100 mm3, 8D2-MMAE, along with vehicle (PBS) and 8D2 control (naked, unconjugated 8D2), were administered by intravenous (IV) injection through the tail vein at 2 mg/kg, once every 10 days. Tumor sizes were measured once per week. As shown in FIG. 6, after treatment with 8D2-MMAE, tumor growth in 2 of the 6 animals was in complete remission.

Example 6—Additional Anti-LGR4 mAbs

Another LGR4 monoclonal antibody (mAb) clone was identified. Additional mAbs in the library were analyzed and it was determined that the clone 3G6 displayed higher affinity (Kd=0.1 ug/ml) than mAb 8D2 (Kd=0.5 ug/ml) in binding to human LGR4 as is shown in FIG. 7.

It was determined that 3G6 was more potent than 8D2 in inhibiting cell survival when combined with a secondary ADC. Serial dilutions of the LGR4 monoclonal antibodies 8D2 or 3G6 were mixed with cells and MMAF-conjugated anti-rat IgG (ratio=1:2). When tested, 3G6 was more potent in inhibiting the growth of cells with high expression of LGR4. As shown in FIG. 8, 3G6 displayed high potency in reducing the growth of the ovarian cancer cell line OVCAR3 cells and HEK293 cells which overexpress LGR4. This suggests that while both LGR4 monoclonal antibodies have activity, 3G6 may be more effective at targeting tumor cells in vivo, thus increasing patient survival.

V. Sequences

The Vh and Vl sequences of 3G6 and 8D2 clone were amplified by PCR, cloned, and sequenced. Their DNA and protein sequences are shown below in Table 1.

TABLE 1

Anti-LGR4 antibody sequences.

| mAb | Heavy Chain Sequence | | | Light Chain Sequence | | |
|---|---|---|---|---|---|---|
|  | CDR1 | CDR2 | CDR3 | CDR1 | CDR2 | CDR3 |
|  | Amino acid sequence | | | Amino acid sequence | | |
|  | Nucleic acid sequence | | | Nucleic acid sequence | | |
| 8D2 | GYTFSTSY (SEQ ID NO: 3) | IYVGAGGP (SEQ ID NO: 4) | ARVRGYAM DA (SEQ ID NO: 5) | QDISTS (SEQ ID NO: 8) | YAS (SEQ ID NO: 9) | QQSYSLPV T (SEQ ID NO: 10) |
|  | QVQLQQSGAELVKPGASVNLSCKTSGY IFSTSYMSWFKQIPGQIIEWVGLIYVG AGGPTYNQKFKGKASLTVDTSSSTAYM DLSSLTAEDSAVYFCARVRGYAMDAWG QGTSVTVSS (SEQ ID NO: 1) | | | DIVLIQSPAILSVIPGESVSLSCRASQ DISTSIHWYQQKSNESPRLLIKYASQS ISGIPSRFSGGGSGTDFTLTINRVESE DFSVYYCQQSYSLPVTFGSGTKLELKR (SEQ ID NO: 6) | | |
|  | CAGGTCCAGCTGCAGCAATCTGGGGCT GAGTTGGTAAAGCCTGGTGCTTCAGTG AATTTGTCCTGCAAGACTTCTGGTTAC ACCTTCAGCACTAGCTACATGAGTTGG TTCAAGCAGATTCCTGGACAGACTATT GAGTGGGTTGGACTGATTTATGTTGGA GCTGGTGGTCCTACCTATAATCAGAAG TTCAAGGGCAAGGCCTCACTTACTGTC GACACATCTTCCAGCACAGCGTACATG GATCTCAGCAGCCTGACAGCTGAGGAC TCTGCAGTCTATTTTTGTGCAAGGGTT CGGGGCTATGCTATGGATGCCTGGGGT CAAGGAACTTCAGTCACCGTCTCCTCA (SEQ ID NO: 2) | | | GACATTGTGCTCACCCAGTCTCCAGCC ACCCTGTCTGTGACTCCAGGAGAGAGT GTGAGTCTCCTGCAGGGCCAGTCAG GATATTAGCACTAGCATTCATTGGTAT CAGCAAAAATCAAATGAGTCTCCAAGG CTTCTCATCAAGTATGCTTCCCAGTCC ATCTCTGGAATCCCCTCCAGGTTCAGT GGAGGTGGATCAGGGACAGATTTCACT CTCACTATCAACAGAGTCGAATCTGAA GATTTTTCAGTTTATTACTGTCAACAG AGTTACAGCTTGCCCGTCACGTTCGGA TCTGGGACCAAGCTGGAACTGAAACGG (SEQ ID NO: 7) | | |
| 3G6 | GYTFTSNF (SEQ ID NO: 13) | IYPGDGDT (SEQ ID NO: 14) | SRSNSGYN WFAY (SEQ ID NO: 15) | QNINKN (SEQ ID NO: 18) | YTN (SEQ ID NO: 19) | YQYRTGWT (SEQ ID NO: 20) |
|  | QVQLQQSGAELVKPGSSVKISCKASGY TFTSNFMHWIKQQPGNGLEWIGWIYPG DGDTDYNQKFIGKATLTADKSSSTAYM QLSSLTSEDSAVYFCSRSNSGYNWFAY WGQGTLVTVSS (SEQ ID NO: 11) | | | DIVLTQSPPVLSASVGDRVTLSCKASQ NINKNLDWYQQKHGEAPKLLIYYTNNL QTGIPSRFSGSGSGTDYTLTIRSLQPE DVATYYCYQYRTGWTFGGGTKLELKR (SEQ ID NO: 16) | | |
|  | CAGGTTCAGCTGCAGCAGTCTGGGGCT GAACTGGTGAAGCCTGGGTCCTCAGTG AAAATTTCCTGCAAGGCTTCTGGCTAC ACCTTCACCAGTAACTTTATGCACTGG ATAAAACAGCAGCCTGGAAATGGCCTT GAGTGGATTGGGTGGATTTATCCTGGA GATGGTGATACAGATTACAATCAAAAG TTCATTGGGAAGGCAACACTCACTGCA GACAAATCCTCCAGCACAGCCTATATG CAGCTCAGCAGCCTGACATCTGAGGAC TCTGCAGTCTATTTCTGTTCAAGATCG AATTCGGGATACAATTGGTTTGCTTAC TGGGGCCAAGGCACTCTGGTCACCGTC TCCTCA (SEQ ID NO: 12) | | | GACATTGTGCTCACCCAGTCTCCTCCA GTCCTGTCTGCATCTGTGGGAGACAGA GTCACTCTCAGCTGCAAAGCAAGTCAG AATATTAATAAGAACTTAGACTGGTAT CAACAAAAGCATGGAGAAGCTCCAAAA CTCCTGATATATTATACAAACAATTTG CAAACGGGTATCCCATCAAGGTTCAGT GGCAGTGGATCTGGTACAGATTACACA CTCACCATCAGAAGCCTGCAGCCTGAG GATGTTGCCACATATTACTGCTATCAG TATAGAACTGGGTGACCTTCGGTGGA GGCACCAAGCTGGAGTTGAAACGG (SEQ ID NO: 17) | | |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Application Nos. 2004/0126828 and 2002/0172677

U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024.

Lefranc et al., *Methods in molecular biology*, 907, 3, 2012.
Haidar et al., *Proteins* 80, 896, March, 2012.
Retter et al., *Nucleic Acids Res* 33, D671, Jan. 1, 2005.
Singer et al., *J Immunol* 150, 2844, 1993.
Yu et al., *PLoS ONE* 5, e9072, 2010.

1. Carter, P. J., and Senter, P. D. (2008) Antibody-drug conjugates for cancer therapy, Cancer J 14, 154-169.
2. Teicher, B. A. (2014) Antibody drug conjugates, Current opinion in oncology 26, 476-483.
3. Leal, M., Sapra, P., Hurvitz, S. A., Senter, P., Wahl, A., Schutten, M., Shah, D. K., Haddish-Berhane, N., and Kabbarah, 0. (2014) Antibody-drug conjugates: an emerging modality for the treatment of cancer, Ann N Y Acad Sci 1321, 41-54.
4. Senter, P. D. (2009) Potent antibody drug conjugates for cancer therapy, Current opinion in chemical biology 13, 235-244.
5. Teicher, B. A. (2009) Antibody-drug conjugate targets, Current cancer drug targets 9, 982-1004.
6. Bander, N. H. (2013) Antibody-drug conjugate target selection: critical factors, Methods Mol Biol 1045, 29-40.
7. Hsu, S. Y., Kudo, M., Chen, T., Nakabayashi, K., Bhalla, A., van der Spek, P. J., van Duin, M., and Hsueh, A. J. (2000) The three subfamilies of leucine-rich repeat-containing G protein-coupled receptors (LGR): identification of LGR6 and LGR7 and the signaling mechanism for LGR7, Mol Endocrinol 14, 1257-1271.
8. Carmon, K. S., Gong, X., Lin, Q., Thomas, A., and Liu, Q. (2011) R-spondins function as ligands of the orphan receptors LGR4 and LGR5 to regulate Wnt/beta-catenin signaling, Proc Natl Acad Sci USA 108, 11452-11457.
9. de Lau, W., Barker, N., Low, T. Y., Koo, B. K., Li, V. S., Teunissen, H., Kujala, P., Haegebarth, A., Peters, P. J., van de Wetering, M., Stange, D. E., van Es, J. E., Guardavaccaro, D., Schasfoort, R. B., Mohri, Y., Nishimori, K., Mohammed, S., Heck, A. J., and Clevers, H. (2011) Lgr5 homologues associate with Wnt receptors and mediate R-spondin signalling, Nature 476, 293-297.
10. Glinka, A., Dolde, C., Kirsch, N., Huang, Y. L., Kazanskaya, O., Ingelfinger, D., Boutros, M., Cruciat, C. M., and Niehrs, C. (2011) LGR4 and LGR5 are R-spondin receptors mediating Wnt/beta-catenin and Wnt/PCP signalling, EMBO Rep 12, 1055-1061.
11. Hao, H. X., Xie, Y., Zhang, Y., Charlat, O., Oster, E., Avello, M., Lei, H., Mickanin, C., Liu, D., Ruffner, H., Mao, X., Ma, Q., Zamponi, R., Bouwmeester, T., Finan, P. M., Kirschner, M. W., Porter, J. A., Serluca, F. C., and Cong, F. (2012) ZNRF3 promotes Wnt receptor turnover in an R-spondin-sensitive manner, Nature 485, 195-200.
12. Carmon, K. S., Gong, X., Yi, J., Thomas, A., and Liu, Q. (2014) RSPO-LGR4 functions via IQGAP1 to potentiate Wnt signaling, Proc Natl Acad Sci USA 111, E1221-1229.
13. de Lau, W., Peng, W. C., Gros, P., and Clevers, H. (2014) The R-spondin/Lgr5/Rnf43 module: regulator of Wnt signal strength, Genes Dev 28, 305-316.
14. Gao, Y., Kitagawa, K., Hiramatsu, Y., Kikuchi, H., Isobe, T., Shimada, M., Uchida, C., Hattori, T., Oda, T., Nakayama, K., Nakayama, K. I., Tanaka, T., Konno, H., and Kitagawa, M. (2006) Up-regulation of GPR48 induced by down-regulation of p27Kip1 enhances carcinoma cell invasiveness and metastasis, Cancer Res 66, 11623-11631.
15. Gugger, M., White, R., Song, S., Waser, B., Cescato, R., Riviere, P., and Reubi, J. C. (2008) GPR87 is an overexpressed G-protein coupled receptor in squamous cell carcinoma of the lung, Dis Markers 24, 41-50.
16. Seshagiri, S., Stawiski, E. W., Durinck, S., Modrusan, Z., Storm, E. E., Conboy, C. B., Chaudhuri, S., Guan, Y., Janakiraman, V., Jaiswal, B. S., Guillory, J., Ha, C., Dijkgraaf, G. J., Stinson, J., Gnad, F., Huntley, M. A., Degenhardt, J. D., Haverty, P. M., Bourgon, R., Wang, W., Koeppen, H., Gentleman, R., Stan, T. K., Zhang, Z., Largaespada, D. A., Wu, T. D., and de Sauvage, F. J. (2012) Recurrent R-spondin fusions in colon cancer, Nature 488, 660-664.
17. Shinmura, K., Kahyo, T., Kato, H., Igarashi, H., Matsuura, S., Nakamura, S., Kurachi, K., Nakamura, T., Ogawa, H., Funai, K., Tanahashi, M., Niwa, H., and Sugimura, H. (2014) RSPO fusion transcripts in colorectal cancer in Japanese population, Mol Biol Rep.
18. Gong, X., Yi, J., Carmon, K. S., Crumbley, C. A., Xiong, W., Thomas, A., Fan, X., Guo, S., An, Z., Chang, J. T., and Liu, Q. J. (2014) Aberrant RSPO3-LGR4 signaling in Keap1-deficient lung adenocarcinomas promotes tumor aggressiveness, Oncogene.
19. Yi, J., Xiong, W., Gong, X., Bellister, S., Ellis, L. M., and Liu, Q. (2013) Analysis of LGR4 Receptor Distribution in Human and Mouse Tissues, PLoS One 8, e78144.
20. Barretina, J., Caponigro, G., Stransky, N., Venkatesan, K., Margolin, A. A., Kim, S., Wilson, C. J., Lehar, J., Kryukov, G. V., Sonkin, D., Reddy, A., Liu, M., Murray, L., Berger, M. F., Monahan, J. E., Morais, P., Meltzer, J., Korejwa, A., Jane-Valbuena, J., Mapa, F. A., Thibault, J., Bric-Furlong, E., Raman, P., Shipway, A., Engels, I. H., Cheng, J., Yu, G. K., Yu, J., Aspesi, P., Jr., de Silva, M., Jagtap, K., Jones, M. D., Wang, L., Hatton, C., Palescandolo, E., Gupta, S., Mahan, S., Sougnez, C., Onofrio, R. C., Liefeld, T., MacConaill, L., Winckler, W., Reich, M., Li, N., Mesirov, J. P., Gabriel, S. B., Getz, G., Ardlie, K., Chan, V., Myer, V. E., Weber, B. L., Porter, J., Warmuth, M., Finan, P., Harris, J. L., Meyerson, M., Golub, T. R., Morrissey, M. P., Sellers, W. R., Schlegel, R., and Garraway, L. A. (2012) The Cancer Cell Line Encyclopedia enables predictive modelling of anticancer drug sensitivity, Nature 483, 603-607.
21. Austin, C. D., De Maziere, A. M., Pisacane, P. I., van Dijk, S. M., Eigenbrot, C., Sliwkowski, M. X., Klumperman, J., and Scheller, R. H. (2004) Endocytosis and sorting of ErbB2 and the site of action of cancer therapeutics trastuzumab and geldanamycin, Mol Biol Cell 15, 5268-5282.

22. Erickson, H. K., Park, P. U., Widdison, W. C., Kovtun, Y. V., Garrett, L. M., Hoffman, K., Lutz, R. J., Goldmacher, V. S., and Blattler, W. A. (2006) Antibody-maytansinoid conjugates are activated in targeted cancer cells by lysosomal degradation and linker-dependent intracellular processing, Cancer Res 66, 4426-4433.

23. Doronina, S. O., Toki, B. E., Torgov, M. Y., Mendelsohn, B. A., Cerveny, C. G., Chace, D. F., DeBlanc, R. L., Gearing, R. P., Bovee, T. D., Siegall, C. B., Francisco, J. A., Wahl, A. F., Meyer, D. L., and Senter, P. D. (2003) Development of potent monoclonal antibody auristatin conjugates for cancer therapy, Nat Biotechnol 21, 778-784.

What is claimed is:

1. An isolated monoclonal antibody, wherein the antibody specifically binds to LGR4 and wherein the antibody comprises:

(a) a first $V_H$ CDR comprising the amino acid sequence of SEQ ID NO: 3;

(b) a second $V_H$ CDR comprising the amino acid sequence of SEQ ID NO: 4;

(c) a third $V_H$ CDR comprising the amino acid sequence of SEQ ID NO: 5;

(d) a first $V_L$ CDR comprising the amino acid sequence of SEQ ID NO: 8;

(e) a second $V_L$ CDR comprising the amino acid sequence of SEQ ID NO: 9; and (f) a third $V_L$ CDR comprising the amino acid sequence of SEQ ID NO: 10.

2. The antibody of claim 1, wherein the antibody comprises:

(i) a $V_H$ domain at least 80% identical to the $V_H$ domain of 8D2 (SEQ ID NO: 1); and a $V_L$ domain at least 80% identical to the $V_L$ domain of 8D2 (SEQ ID NO: 6).

3. The antibody of claim 2, wherein the antibody comprises a $V_H$ domain identical SEQ ID NO: 1 and a $V_L$ domain identical to SEQ ID NO: 6.

4. The antibody of claim 2, wherein the antibody comprises a $V_H$ domain at least 95% identical to the $V_H$ domain of 8D2 (SEQ ID NO: 1) and a $V_L$ domain at least 95% identical to the $V_L$ domain of 8D2 (SEQ ID NO: 6).

5. The antibody of claim 1, wherein the antibody is recombinant.

6. The antibody of claim 1, wherein the antibody is an IgG, IgM, IgA or an antigen binding fragment thereof.

7. The antibody of claim 1, wherein the antibody is conjugated to an imaging agent, a chemotherapeutic agent, a toxin or a radionuclide.

8. The antibody of claim 7, wherein the antibody is conjugated to a toxin.

9. The antibody of claim 8, wherein the toxin is auristatin.

10. A composition comprising the antibody of claim 1 in a pharmaceutically acceptable carrier.

11. A method for treating a subject having a cancer which expresses LGR4, comprising administering a pharmaceutically effective amount of an antibody of claim 1 to the subject.

* * * * *